(12) United States Patent
Honda et al.

(10) Patent No.: US 7,923,024 B2
(45) Date of Patent: Apr. 12, 2011

(54) MINERAL COMPOSITION

(75) Inventors: Naoteru Honda, Yokkaichi (JP);
Kazuaki Sakaguchi, Yokkaichi (JP);
Katsuyasu Nakata, Yokkaichi (JP);
Hironobu Nanbu, Yokkaichi (JP)

(73) Assignee: Taiyo Kagaku Co., Ltd., Yokkaichi (JP)

( * ) Notice: Subject to any disclaimer, the term of this patent is extended or adjusted under 35 U.S.C. 154(b) by 1181 days.

(21) Appl. No.: 10/563,810

(22) PCT Filed: Jul. 10, 2003

(86) PCT No.: PCT/JP03/08750
§ 371 (c)(1),
(2), (4) Date: Jan. 9, 2006

(87) PCT Pub. No.: WO2005/004640
PCT Pub. Date: Jan. 20, 2005

(65) Prior Publication Data
US 2006/0210608 A1    Sep. 21, 2006

(51) Int. Cl.
*A61K 47/00*    (2006.01)
*A61K 47/06*    (2006.01)

(52) U.S. Cl. ........................................ 424/439

(58) Field of Classification Search .................. None
See application file for complete search history.

(56) References Cited

U.S. PATENT DOCUMENTS

| | | | | |
|---|---|---|---|---|
| 6,074,675 A * | 6/2000 | Nanbu et al. | | 426/74 |
| 6,808,726 B2 * | 10/2004 | Hojo et al. | | 426/74 |
| 7,264,834 B2 * | 9/2007 | Hojo et al. | | 426/74 |
| 2003/0021994 A1 * | 1/2003 | Kawamoto et al. | | 428/402 |
| 2004/0234651 A1 | 11/2004 | Hojo et al. | | |

FOREIGN PATENT DOCUMENTS

| | | |
|---|---|---|
| CN | 1231582 A | 10/1999 |
| JP | 56-117753 A | 9/1981 |
| JP | 57-033540 B2 | 2/1982 |
| JP | 57-110167 A | 7/1982 |
| JP | 61-015645 A | 1/1986 |
| JP | 63-173556 A | 7/1988 |
| JP | 05-319817 A | 12/1993 |
| JP | 06-127909 A | 5/1994 |
| JP | 06-127939 A | 5/1994 |
| JP | 7-284383 A | 10/1995 |
| JP | 09-191855 A | 7/1997 |
| JP | 9-238645 A | 9/1997 |

(Continued)

OTHER PUBLICATIONS

Kumar et al. Preparation and surfactant properties of diglycerol esters of fatty acids; JOACS vol. 66, No. 1. Jan. 1989.*

*Primary Examiner* — Robert A Wax
*Assistant Examiner* — Melissa S Mercier
(74) *Attorney, Agent, or Firm* — Birch, Stewart, Kolasch & Birch, LLP

(57) ABSTRACT

The present invention relates to a mineral composition, characterized in that the mineral composition comprises 100 parts by weight of a metal salt having a solubility product in water at 25° C. of $1.0 \times 10^{-7}$ or less and 0.5 to 50 parts by weight of an emulsifier having an HLB of 6 to 10, wherein the metal salt comprises fine particles having an average particle size of 0.05 to 1 μm.

18 Claims, 1 Drawing Sheet

FOREIGN PATENT DOCUMENTS

| | | |
|---|---|---|
| JP | 10-225263 A | 8/1998 |
| JP | 3050921 B2 | 3/2000 |
| JP | 2000-102365 A | 4/2000 |
| JP | 2001-29052 A | 2/2001 |
| JP | 2001-61443 A | 3/2001 |
| WO | WO-98/08401 A1 | 3/1998 |
| WO | WO-98/14072 B2 | 4/1998 |
| WO | WO-98/35565 A1 | 8/1998 |
| WO | WO-03/026446 A1 | 4/2003 |

\* cited by examiner

MINERAL COMPOSITION

TECHNICAL FIELD

The present invention relates to a mineral composition used as a mineral supplement in the food product field and the like.

BACKGROUND ART

In recent years, insufficient mineral intake has been pointed out. In relation to prevention of the life-style related diseases, which is considered to be caused by mineral deficiency, health maintenance and the like, roles of various kinds of minerals have started to be emphasized. Under such circumstances, mineral-enriched foods have been increasingly found in the market.

For example, calcium is generally contained only in restricted groups of foods, and therefore the intake thereof is apt to be insufficient. In particularly, osteoporosis, which is a bone deterioration disease, has become a major problem in all the countries of the world in recent years. As a method for calcium enrichment in foods, there are known a method of adding water-soluble calcium such as calcium chloride and calcium lactate, and a method of adding water-insoluble calcium such as calcium carbonate and calcium phosphate.

However, when a water-soluble mineral is added, mineral ions are produced in the solution, so that the flavors of the mineral-containing foods are significantly destroyed by salty taste, bitter taste, astringent taste and the like ascribed to the anions. In addition, there have been problems, including a problem that mineral ions may react with proteins to produce coagulated matter, and may have an adverse effect on the organization or physical properties of the food by reacting with an ingredient in the food. Also, when a water-insoluble mineral is added, there have been problems, including a problem that it is difficult to attain homogenization in foods, for example, precipitation and separation occurs in a short period time due to the high specific gravity, or secondary aggregation of powder of the mineral occurs.

Iron is known to be present in a form bound with a blood protein hemoglobin. Under iron-deficient conditions, iron is compensated from stored iron in the tissues. The condition where stored iron is deficient is called latent anemia, which is a worldwide problem from developing countries to advanced countries. This trend is noticeably found particularly in female senior high school students and young adult females, so that there are many women who develop iron deficiency anemia. A major reason for this is thought to be from daily diet. In the case of women, a characteristic reason is that women are under circumstances to easily develop anemia due to iron deficiency resulting from, for example, menstrual bleeding, increase in required iron during pregnancy, insufficient intake due to being on a diet. In order to compensate this iron deficiency, iron-enriched foods have been commercially available, and many commercial products including milk and soft drinks enriched with iron have been commercially available. For example, in soft drinks and the like for the purpose of iron enrichment, a water-soluble iron such as iron lactate, ferrous gluconate and iron sodium cirtrate, or water-insoluble iron such as ferric pyrophosphate is used. However, since water-insoluble iron has a strong iron taste, which is sensuously problematic, there has been a problem that a large quantity could not be used at a time. In addition, since the iron ionized due to the water-solubility is highly reactive to the stomach wall, there has been a problem that a water-soluble iron may be causative of an ulcer and the like in the case where a water-soluble iron is excessively taken into the body. Also, since a water-soluble iron is highly reactive to the other components in a beverage, there has been a problem that precipitation, aggregation, coloration and the like of the reactants occur. Also, in the case of water-insoluble irons, although a problem of the iron taste is overcome, still there has been a problem that it was not preferable in terms of nice external appearance as food products and the bioabsorbability was poor because the specific gravity was as high as 2.75 or more, so that the iron was precipitated in a short period of time when added and dispersed in a beverage.

Magnesium is present in the bones, muscles or other soft tissues in a living body, and about 60% is said to be present in the bones. Magnesium has actions to modulate enzymes, produce energy, regulate protein synthesis and other actions, and it is indicated that serious symptomatic changes in the organs may come out due to deficiency in magnesium intake. A food additive which can be added to foods to enrich magnesium includes inorganic salts such as magnesium chloride and magnesium sulfate, however, these inorganic magnesium salts give a bitter taste, and present a problem that aggregation or precipitation occurs during the manufacturing of processed foods.

Also, zinc is found to activate 20 kinds or more of enzymes including alkaline phosphatases, alcohol dehydroganases and the like, or to be involved in protein synthesis, nucleic acid metabolism, insulin synthesis and the like. In addition, it is known that alimentary deficiency in zinc leads to a disorder in the human body.

As described above, minerals, particularly calcium, iron, magnesium and zinc as mentioned above, have an important role in health maintenance. As such, these minerals are desirably taken in daily diet, but cannot be sufficiently taken under the current diet life of men of today.

In view of this, an attempt was made to develop mineral-enriched foods. However, mineral supplements used for manufacturing such foods have many problems on the basis of the fact that a characteristic property, that is, bioavailability (ratio of the amount absorbed in the living body to the intake amount) of minerals is low, or on the basis of the properties to react with other components or to precipitate in the food.

In the case where a water-soluble mineral is added to foods as a mineral supplement, for example, the flavors of the mineral-containing foods are significantly destroyed by salty taste, bitter taste, astringent taste and the like ascribed to mineral ions produced in the solution, in particular the anions. In addition, there are problems, including a problem that the mineral ions may react with proteins to produce a coagulated matter, and may have an adverse effect on the organization or physical properties of the food by reacting with an ingredient in the food.

Also, when a water-insoluble mineral is added, there is a problem that it is difficult to attain homogenization in foods, for example, precipitation and separation occurs in a short period time due to high specific gravity, or secondary aggregation of powder of the mineral occurs.

Since the water-insoluble mineral generally has a high specific gravity (usually 1.5 or more), the water-insoluble mineral is easily precipitated. Therefore, in order to stably disperse the water-insoluble mineral in water, it is necessitated that the water-insoluble mineral is firstly made into fine particles. In physical crushing methods using a ball mill, jet mill or the like (JP-A-Sho-57-110167), there is a limitation in obtaining fine particles having a particle size in the order of several microns, so that sufficiently stable dispersion is not obtained. As to methods for preparing fine particles having particle sizes in the order of submicrons, there have been numerously reported chemical production methods utilizing reactions for forming salts by neutralization. According to this method, there can be produced ultrafine particles having a particle size of 1/100 microns. However, the resulting ultrafine particles are immediately formed into secondary aggregates after its production, so that there poses a problem in forming coarse particles having particle sizes in the order of microns.

As a method for suppressing the formation of such coarse particles, there have been proposed methods for adsorbing and retaining primary fine particles in the network structure of polymer by adding a mucopolysaccharide such as a crystalline cellulose, pectin, carageenan and guar gum (JP-A-Sho-56-117753, JP-B-Sho-57-35945 and JP-A-Hei-09-191855); methods of alleviating specific gravity by adding a water-insoluble mineral to fats and oils and dispersing the water-insoluble mineral therein, adjusting the content of the fats and oils in the resulting mixture so as to have the content to be 30% by weight or more (JP-A-Sho-57-110167); and the like. In any of these methods, however, since it is needed to add large amounts of the substances other than the targeted water-insoluble mineral, there are defects in that the solute dispersed therein is diluted, and that the dispersibility of the water-insoluble mineral is drastically lowered. As to methods for eliminating the above defects, there have been developed a method for treating surfaces of fine particles of a water-insoluble mineral with an organic acid or an alkaline agent (JP-A-Sho-61-15645); a method of treating with a surfactant, such as sucrose ester (JP-A-Sho-63-173556 and JP-A-Hei-5-319817), and the like. In the former method, however, there is a defect in that the metal ions and the like constituting the water-insoluble mineral are likely to be made into free ions in the water phase. In addition, in the latter method, there are defects in that the surfactant layer formed by adsorption to the surfaces of the fine particles is peeled off when subjected to a heat treatment such as sterilization, and that secondary aggregation is accelerated.

Also, there have been proposed a process for preparing a calcium carbonate dispersion by formulating a hydrophilic emulsifier having an HLB of 10 or more to an aqueous calcium suspension, and grinding the mixture using a wet grinder (JP-A-Hei-06-127939), a process for preparing a calcium carbonate dispersion by formulating a hydrophilic emulsifier having an HLB of 10 or more to an aqueous calcium phosphate suspension, and grinding the mixture using a wet grinder (JP-A-Hei-06-127909), and the like. The main purpose of these processes is to prevent secondary aggregation of powder. Although these methods improve the dispersibility upon addition to food, the effect to retain the dispersibility for a long period of time is insufficient in foods to which the dispersion is added, in particular liquid foods. In addition, the hydrophilicity of the emulsifier to be added is high, and a large amount of bubbles are formed when a homogenizer is used or agitation is performed after the emulsifier is dissolved in an aqueous phase, which was problematic to the subsequent operation. In addition, for a highly hydrophilic emulsifier, even when a layer of the emulsifier is once formed by adsorption to the surface of the particles, the emulsifier is easily dissolved in the water solvent by monodispersion or micelle formation, so that secondary aggregation could not be completely prevented.

Further, with respect to the bioabsorbability of mineral, not all the minerals mentioned above are completely absorbed and the bioavailability is in the order of about a few percent to a few tens percent, there has been a problem that most of the minerals are excreted without being available in the living body. Due to the above-mentioned dispersing techniques of formulating a mucopolysaccharide, a hydrophilic emulsifier or the like to finely grained mineral, there is found an effect of improvement in dispersion stability to some extent, but not completely, as compared with finely grained mineral not formulated with a mucopolysaccharide or a hydrophilic emulsifier. However, after being added to mineral-enriched food and taken into the body, an improvement in bioabsorbability, that is bioavailability, could not be expected considering the properties of the above mucopolysaccharide and the like to be formulated. Because a mucopolysaccharide prevents secondary aggregation by supporting finely grained mineral in its three-dimensional network structure which provides steric hindrance but does not have any effect on the absorption of finely grained mineral. Also, the hydrophilic emulsifier prevents the secondary aggregation by forming a coating on the surface of finely grained minerals. However, when added to a mineral enriched food, since the material constituting the coating is hydrophilic, the coating is easily peeled off and transferred to the aqueous phase. Hydrophilic polyglycerol fatty acid esters, sugar esters and the like have a large molecular weight, and a low biocompatibility due to a large difference in polarity therebetween, as compared with molecules constituting the biomembrane, such as phospholipids. On the other hand, in minerals prepared by coating with phospholipids such as lethitin, since the electric charges from the functional groups of the phospholipids tend to form a salt together with the charges possessed by the mineral, coarse mass of the prepared particles due to secondary aggregation is likely to be produced, so that it was difficult to finely grain and formulate the particles. In addition, there has been proposed a method for improving dispersion stability by formulating an enzymatically decomposed lecithin with a mineral composition (Japanese Patent No. 3050921). In this method, it is difficult to control the fineness of particles due to the influence of the charges from the functional groups of phospholipids. For a water-insoluble mineral prepared by formulation an enzymatically decomposed lecithin during the special reaction for forming salt by neutralization, the dispersion stability is relatively improved. However, since a highly hydrophilic nonionic surfactant is formulated as an emulsifier coating, the coating is peeled off and transferred to the aqueous phase due to the dilution of the emulsifier upon addition to food. Therefore, it could not be sufficiently expected that the absorbability in the body in the intestinal tract was improved.

DISCLOSURE OF INVENTION

As described above, conventionally, it was difficult to prepare a mineral supplement, which is excellent in bioabsorbability, that is bioavailability, of mineral, without producing coarse mass of mineral particles due to secondary aggregation, which is excellent in handling during manufacturing as well as dispersibility and dispersion stability in aqueous phase, and which has substantially no influence on the taste, color, physical properties and the like of the foods and the like when added thereto. Therefore, an object of the present invention is to provide a mineral composition which possesses various properties required for mineral supplement and can be suitably used as a mineral supplement.

Specifically, the present invention relates to:

[1] a mineral composition, characterized in that the mineral composition comprises 100 parts by weight of a metal salt having a solubility product in water at 25° C. of $1.0 \times 10^{-7}$ or less and 0.5 to 50 parts by weight of an emulsifier having an HLB of 6 to 10, wherein the metal salt comprises fine particles having an average particle size of 0.05 to 1 μm;

[2] the mineral composition according to the above [1], wherein the emulsifier is a diglycerol fatty acid ester;

[3] the mineral composition according to the above [2], wherein the diglycerol fatty acid ester comprises 50% by weight or more of the monoesters;

[4] the mineral composition according to any one of the above [1] to [3], wherein the metal salt is at least one member selected from metal salts comprising calcium, magnesium, iron or zinc; and

[5] a food or beverage comprising the mineral composition as defined in any one of the above [1] to [4].

BEST MODE FOR CARRYING OUT THE INVENTION

Figure 1:
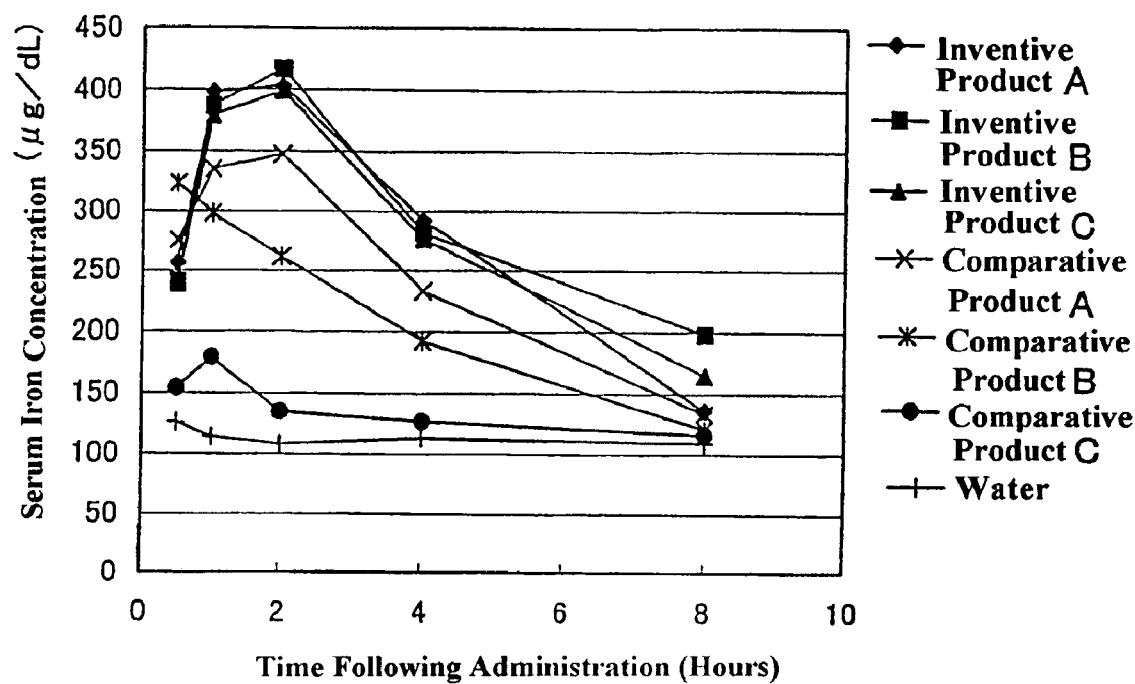
FIG. 1 is a graph showing changes in concentration of serum iron (iron contained in the serum) over time (0.5 to 8 hours following administration) when each one of the inventive products A to C, the comparative products A to C and water was administered to the rats.

One of great features of the mineral composition of the present invention (hereinafter referred to as the composition) is that the mineral composition comprises a metal salt having a solubility product in water at 25° C. of $1.0 \times 10^{-7}$ or less and an emulsifier having an HLB of 6 to 10, wherein the content of the emulsifier is 0.5 to 50 parts by weight based on 100 parts by weight of the metal salt, and the metal salt comprises fine particles having an average particle size of 0.05 to 1 μm.

The composition comprises fine particles of a metal salt having a very small average particle size. Generally, on the surface of fine particles of the metal salt, an adsorption layer by the emulsifier mentioned above is formed (hereinafter, fine particles of a metal salt having an adsorption layer (coating) by the emulsifier may be simply referred to as fine metal particles). The adsorption layer is stable. For instance, the adsorption layer is not peeled off during storage at normal temperatures (25° C.) and even when subjected to a heat treatment, so that secondary aggregation of the fine metal particles contained in the composition is effectively inhibited. Consequently, a good dispersibility is obtained when the composition is added, for instance, to foods or beverages. Further, the fine metal particles in the composition are excellent in dispersion stability because the fine metal particles are finely grained and because the specific gravity of the emulsifier used is generally lower than that of water. Therefore, the composition itself, or foods and the like (especially those in the liquid form) to which the composition is added have an excellent storage stability.

The emulsifier having an HLB of 6 to 10, which is contained in the composition of the present invention, is relatively lipophilic, so that less foaming occurs when the agent is dissolved in an aqueous phase, which provides an excellent handling. In addition, minerals (metal components originated from the metal salt) contained in the composition are excellent in bioabsorbability, or bioavailability. In other words, it is presumed that, in the stomach, dissolution of minerals into the gastric acid is prevented due to the effect of coating the metal salt by the adsorption layer of the emulsifier having an HLB of 6 to 10. After transferred to the intestines, it is presumed that since the sizes and polarities of the molecules of the emulsifier are, generally, almost the same as those of the constituent molecules of the cell membrane of the intestinal epithelial cells involved in the absorption, that is phospholipids, the affinity of the fine metal particles to the cell membrane is increased, thereby increasing the bioabsorbability. Also, since the coating of the emulsifier is relatively stable, the effect of sustained-release of mineral will be exhibited.

Further, the metal salt contained in the composition of the present invention is substantially water-insoluble. In addition, due to the effect of coating by the above-mentioned emulsifier, when the composition is added, for instance, to the foods or beverages, there is no generation of mineral ions or anionic ions. Therefore, there is no strange taste caused by the ions and no production of coagulations or color development caused by a reaction between the ions and the components in the foods and the like, and there is no stimulation to the mucosa of the digestive tract such as the gastric wall in an individual.

Incidentally, in the present specification, "water-insoluble mineral" refers to a mineral-containing substance which is substantially water-insoluble, and also includes mineral-containing substances which are hardly soluble in water (water-hardly-soluble minerals).

The metal salt in the present invention comprises a water-insoluble mineral having a solubility product in water at 25° C. of $1.0 \times 10^{-7}$ or less, preferably $1.0 \times 10^{-8}$ or less, more preferably $1.0 \times 10^{-10}$ or less, and are in the form of fine particles having an average particle size of 0.05 to 1 μm, preferably 0.05 to 0.5 μm, more preferably 0.1 to 0.3 μm.

In the present specification, the "solubility product" is a product of molar concentrations (mol/liter) of cations and anions in a saturated solution of metal salts. Among the solubility products and general solubilities, there is a correlation shown by the following equation. Specifically, when the metal salt is denoted by $M_a X_b$, wherein M and X denote electrolyte components, and a and b denote coefficients of M and X, respectively; and the solubility is denoted by S, the solubility product (Ksp) is expressed by the equation:

$$Ksp = [M]^a [X]^b = (aS)^a \times (bS)^b = a^a \times b^b \times S^{(a+b)}$$

wherein inside the parentheses [ ] denotes ion densities expressed as mol/liter.

Taking calcium carbonate ($CaCO_3$) as one example, Ksp of $CaCO_3$ is $4.7 \times 10^{-9}$ in water at 25° C. When the values are plugged into the equation, the equation reads: $[Ca]^1 [CO_3]^1 = S^2 = 4.7 \times 10^{-9}$. The solubility S of $CaCO_3$ is about $6.9 \times 10^{-5}$ mol/liter (6.9 ppm), so that $CaCO_3$ is generally considered a water-insoluble salt. Metal salts having a solubility nearly equal to or less than that of $CaCO_3$ can be clearly said to be water-insoluble.

From the above equation, the solubility of metal salts having a solubility product in water at 25° C. of more than $1.0 \times 10^{-7}$ is about $3.2 \times 10^{-3}$ mol/liter, which is about 100 times as large as the solubility of $CaCO_3$, so that the metal salts having such a solubility are not water-insoluble in a strict sense. The reason for this is that by a slight change of pH in the water phase containing the metal salts, the surface of the insoluble salt is likely to be unstable, which may cause the dissolution. Consequently, when such metal salts are used, the desired effects of the present invention may not be sufficiently exhibited.

Therefore, the metal salt used in the present invention is required to have a solubility product in water at 25° C. of $1.0 \times 10^{-7}$ or less.

The metal salt in the present invention is not particularly limited. For instance, the metal salts include silver chloride (AgCl, a solubility product in water at 25° C.: $1.0 \times 10^{-10}$); silver pyrophosphate ($Ag_4P_2O_7$, a solubility product in water at 25° C.: $1.0 \times 10^{-21}$); aluminum hydroxide ($Al(OH)_2$, a solubility product in water at 25° C.: $2.0 \times 10^{-32}$); aluminum phosphate ($AlPO_4$, a solubility product in water at 25° C.: $5.8 \times$ $10^{-19}$); barium sulfate (BaSO$_4$, a solubility product in water at 25° C.: $1.0 \times 10^{-10}$); barium phosphate (Ba$_3$(PO$_4$)$_2$, a solubility product in water at 25° C.: $6.0 \times 10^{-39}$); barium carbonate (BaCO$_3$, a solubility product in water at 25° C.: $5.1 \times 10^{-9}$); calcium pyrophosphate (Ca$_2$P$_2$O$_7$, a solubility product in water at 25° C.: $2.0 \times 10^{-19}$); calcium phosphate (Ca$_3$(PO$_4$)$_2$, a solubility product in water at 25° C.: $2.0 \times 10^{-29}$); calcium carbonate (CaCO$_3$, a solubility product in water at 25° C.: $4.7 \times 10^{-9}$); ferrous hydroxide (Fe(OH)$_2$, a solubility product in water at 25° C.: $8.0 \times 10^{-16}$); ferrous phosphate (Fe$_3$(PO$_4$)$_2$, a solubility product in water at 25° C.: $1.3 \times 10^{-22}$); ferric pyrophosphate (Fe$_4$(P$_2$O$_7$)$_3$, a solubility product in water at 25° C.: $2.0 \times 10^{-13}$); ferrous carbonate (FeCO$_3$, a solubility product in water at 25° C.: $3.5 \times 10^{-11}$); magnesium hydroxide (Mg(OH)$_2$, a solubility product in water at 25° C.: $1.1 \times 10^{-11}$); magnesium pyrophosphate (Mg$_2$P$_2$O$_7$, a solubility product in water at 25° C.: $2.5 \times 10^{-13}$); magnesium phosphate (Mg$_3$(PO$_4$)$_2$, a solubility product in water at 25° C.: $2.0 \times 10^{-27}$); magnesium oxide (MgO, a solubility product in water at 25° C.: $1.0 \times 10^{-7}$); cupric carbonate (CuCO$_3$, a solubility product in water at 25° C.: $2.5 \times 10^{-10}$); manganese hydroxide (Mn(OH)$_2$, a solubility product in water at 25° C.: $1.6 \times 10^{-13}$); manganese sulfate (MnSO$_4$, a solubility product in water at 25° C.: $1.0 \times 10^{-11}$); nickel hydroxide (Ni(OH)$_2$, a solubility product in water at 25° C.: $2.7 \times 10^{-15}$); nickel phosphate (Ni$_3$(PO$_4$)$_2$, a solubility product in water at 25° C.: $4.5 \times 10^{-10}$); lead sulfate (PbSO$_4$, a solubility product in water at 25° C.: $1.7 \times 10^{-8}$); lead phosphate (Pb$_3$(PO$_4$)$_2$, a solubility product in water at 25° C.: $1.5 \times 10^{-13}$); zinc oxide (ZnO, a solubility product in water at 25° C.: $2.7 \times 10^{-9}$); zinc hydroxide (Zn(OH)$_2$, a solubility product in water at 25° C.: $7.0 \times 10^{-18}$); zinc pyrophosphate (Zn$_2$P$_2$O$_7$, a solubility product in water at 25° C.: $2.0 \times 10^{-8}$); and the like. Incidentally, solubility products in water at 25° C. of various water-insoluble minerals are described, for example, in Kagaku Binran: Kisohen I (revised 5th eddition) [published by Maruzen]. These metal salts can be used alone or in admixture of two or more kinds.

Among the metal salts as listed above, phosphate salts, carbonate salts, iron salts, calcium salts and magnesium salts are preferable, and iron salts are more preferable, from the viewpoint of stable dispersion when added and mixed with foods for the purpose of nutrition enrichment. In terms of minerals contained in the metal salt, the metal salt is preferably at least one member selected from metal salts containing calcium, magnesium, iron or zinc, from the viewpoint of being preferable for nutrition enrichment of food.

Specifically, in the composition of the present invention, preferably used are, for example, a water-insoluble calcium including calcium carbonate, calcium phosphate and the like; a water-insoluble magnesium including magnesium phosphate, magnesium oxide and the like; a water-insoluble iron including ferric pyrophosphate and the like; a water-insoluble zinc including zinc hydroxide, zinc pyrophosphate, zinc oxide and the like. In particular, magnesium phosphate, ferric pyrophosphate and calcium phosphate are preferably used. Incidentally, as a water-insoluble magnesium, dolomite having a MgCO$_3$.CaCO$_3$ composition also is preferably used.

In addition, based on the Stokes' theorem, in order for a water-insoluble mineral having a high specific gravity to be stably dispersed, the mineral is required to be fine particles having an average particle size of 2 microns or less. Since the fine particles of the metal salt in the present invention have an average particle size of 0.05 to 1 µm, sufficient dispersion stability can be exhibited even in the case where the coating by the emulsifier is present. Incidentally, the average particle size of the fine metal particles is preferably from 0.05 to 0.5 µm, more preferably from 0.1 to 0.3 µm.

In the present specification, the "average particle size" can be measured using, for example, an LS particle size distribution analyzer such as an LS series MODE LS 230 manufactured by Beckman Coulter, Inc.

As the method for preparing a metal salt having an average particle size within the desired ranges mentioned above, for instance, a physical crushing method or a method for forming salt by neutralization is preferable.

In the physical crushing method, a metal salt having the desired average particle size can be obtained by physically grinding metal salt using, for example, a wet grinder such as Dyno-Mill, Sand Mill and Cobol Mill, an emulsification/dispersion apparatus such as Nanomizer, Microfluidizer and a homogenizer, an ultrasonic disperser, and the like. On the other hand, as a method for forming salt by neutralization, there are known a method using a neutralization reaction between a strong acid and a strongly basic salt, a method using a neutralization reaction between a weak acid and a strongly basic salt, and other methods [Nihon no Shokuhin Kikai Souran (see Nihon Shokuhin Kikai Kogyo Corp.) Hyojun Kiso Kagaku, Chapter 6, Reaction between Acid and Base, published in November, 2002]. Examples of the former method include a method for obtaining ferric pyrophosphate [Fe$_4$(P$_2$O$_7$)$_3$] by a neutralization reaction between ferric chloride (FeCl$_3$) and tetrasodium pyrophosphate [Na$_4$(P$_2$O$_7$)], and examples of the latter method include a method of obtaining calcium phosphate (Ca$_3$(PO$_4$)$_2$ by neutralization reaction between phosphoric acid (H$_3$PO$_4$) and calcium hydroxide [Ca(OH)$_2$].

According to these methods, although ultrafine particles with a particle size of about 0.01 to 0.1 µm were produced as primary particles, a secondary aggregation occurred, and the resulting product was collected as aggregates with a particle size of approximately 0.2 to 2 µm. Therefore, it is preferable that fine particles of the metal salt, which are prepared so that the average particle size is the desired value by these methods, are used, immediately after their preparation, for preparing the composition of the present invention. By doing so, secondary aggregation of the primary particles is effectively suppressed, thereby retaining the shape of the primary particles.

The emulsifier in the present invention is not particularly limited, as long as the agent has an HLB of 6 to 10. The HLB is preferably from 6 to 9, more preferably from 7 to 9. The emulsifiers having an HLB of 6 to 10 can be used alone or as a mixture. In addition, in the case of the mixture, an emulsifier having an HLB outside the range of 6 to 10 may be contained, and the average value of the HLB values of the emulsifiers contained in the mixture of emulsifiers (that is, the value obtained by dividing the sum of the HLB values of the individual emulsifier molecules by the number of the molecules of all the emulsifiers contained in the mixture) should be within the range of 6 to 10.

In the present specification, HLB is a measure indicating the degree of hydrophilicity and lipophilicity (hydrophobicity) of an emulsifier. Those with higer hydrophilicity give higher values. In the present invention, from the viewpoint of securing the formation of stable adsorption layer by the emulsifier on the surface of the fine particles of the metal salt, a relatively highly lipophilic (hydrophobic) emulsifier is used.

The HLB is calculated using the Griffin equation shown below:

$$HLB = 20 \times \frac{\text{Molecular Weight of Hydrophilic Part}}{\text{Molecular Weight of Whole Emulsifier}}$$

The hydrophilic part in the above equation refers to the part in which hydrocarbon chains are excluded from the whole molecule constituting an emulsifier.

The kind of the emulsifier of the present invention is not particularly limited, as long as the desired effects of the present invention can be exhibited, and cationic, anionic or amphoteric ones, or nonionic ones can be used. Among them, nonionic ones are more preferable. The reasons why relatively lipophilic, nonionic emulsifiers are effective are that the emulsifier adsorbed on the surface of fine particles of metal salt is kept adsorbed due to its lipophilicity, without being dissolved or desorbed into the aqueous phase, and that the specific gravity of the emulsifier is generally lower than the specific gravity of water.

The above-mentioned ionic emulsifiers include, for example, glycerol organic acid fatty acid ester such as glycerol succinic acid myristic acid ester, and the like.

The above-mentioned nonionic emulsifiers include, for example, polyglycerol fatty acid ester, glycerol fatty acid ester, sucrose fatty acid ester, and the like. As the emulsifier of the present invention, polyglycerol fatty acid ester is preferable.

As the polyglycerol fatty acid ester, preferable are those having an average polymerization degree of glycerol of about 3 to 10 and an average esterification ratio of about 5 to 30%. The constituent fatty acid is not particularly limited, and may be a linear or branched, saturated or unsaturated fatty acid. In addition, the kind of the constituent fatty acid is not particularly limited, and one or more fatty acids may be contained in one polyglycerol fatty acid ester. Incidentally, the above-mentioned average esterification ratio is expressed in percentage of the average number of ester bonds to the average number of total hydroxyl groups per one mole of polyglycerol. The average of total numbers of hydroxyl groups is expressed as n +2 when the average polymerization degree is n.

As the polyglycerol fatty acid ester, among others, diglycerol fatty acid esters are especially preferable. As the constituent fatty acid of diglycerol fatty acid esters, a saturated or unsaturated fatty acid having preferably 8 to 22 carbon atoms, more preferably 10 to 14 carbon atoms is preferable. Also, the same or different fatty acids may be bonded via an ester bond to a hydroxyl group in any position of the diglycerol. Preferably, the same or different fatty acids are bonded via an ester bond to the hydroxyl groups in both ends of the diglycerol and, more preferably, a fatty acid is bonded via an ester bond to the hydroxyl group on one end of the diglycerol. The constituent fatty acid thereof includes, for example, lauric acid, myristic acid, palmitic acid, stearic acid, oleic acid, capric acid, isostearic acid, and the like.

The emulsifier of the present invention may be a commercially available one or may be one synthesized according to the known methods, and those with higher purity are preferable.

For instance, in the case where the diglycerol fatty acid ester mentioned above is synthetically obtained, it is preferable to use as a raw material that highly purified diglycerol which contains no other molecules but those having a polymerization degree of glycerol of 2. Since such diglycerol does not have the distribution of polymerization degree as found in polyglycerols, the desired diglycerol fatty acid ester is easily obtained. Incidentally, when a less purified diglycerol is used in an initial stage, the resulting product may be appropriately purified according to the known methods after the ester synthesis.

On the other hand, even in the case where a highly purified diglycerol is used, 4 kinds of esters, the monoesters, diesters, trimester and tetraester are produced when the esterification reaction is carried out under the conventional conditions. In the case of a diglycerol fatty acid ester prepared with appropriately optimizing the reaction composition, the diglycerol fatty acid ester without purification can be directly used after the synthesis, however, it is preferable to use highly purified monoesters only. Specifically, as the diglycerol fatty acid ester, preferable are those which have a monoester content of 50% by weight or more, more preferably 70% by weight or more.

The diglycerol fatty acid esters, particularly monoesters, especially preferably used as the emulsifier of the present invention are markedly excellent in property to adsorb to the surface of fine particles of the metal salt and property to cover the surface (hereinafter referred to as adsorptive covering properties), as compared with the other nonionic emulsifiers such as sucrose fatty acid ester and glycerol fatty acid ester. The factors for the high adsorptive covering properties is that the diglycerol fatty acid ester has a surface activating action, so that the ability to lower surface tension by aggregating between the interfaces is very high, as compared with the other nonionic emulsifiers.

Generally, the polyglycerol fatty acid esters and the sucrose fatty acid esters have a distribution based on the polymerization degree and esterification, and will be present as a mixture of various compounds ranging from those with excellent quality to those with poor quality. For instance, in the case where one in an unpurified form immediately after the synthesis is used, a sufficiently stable adsorption layer may not be formed on the surface of fine particles of the metal salt. Since diglycerol fatty acid ester are relatively small molecules, it is easy to purify a single kind of the ester components to a high degree on an industrial scale, so that only esters with excellent quality can be obtained in a high purity. It can be said that the reason why diglycerol fatty acid esters are effective as an emulsifier in the present invention is that they are easy to handle, in addition to their own properties as described above.

As described above, when a relatively lipophilic emulsifier is used, a stable adsorption layer can be generally formed on the surface of fine particles of the metal salt. In the case where a highly purified diglycerol fatty acid ester, preferably a diglycerol fatty acid ester having a monoester content of 50% by weight or more is used, it is presumed that there are less esterified products other than monoester which are considered to act to prevent formation of the adsorption layer in the interface between the esters and the surface of fine particles of the metal salt when the esters are adsorbed to the surface to form the adsorption layer, so that diglycerol fatty acid monoester is densely adsorbed in multiple layers, thereby increasing the thickness of the adsorption layer and thus stabilizing the layer.

In the composition of the present invention, a part or all of the surface of fine particles of the metal salt is coated by the layer of the above-mentioned emulsifier. Therefore, the amount ratio between the above-mentioned metal salt and the above-mentioned emulsifier is important. The composition of the present invention comprises 0.5 to 50 parts by weight, preferably from 1 to 40 parts by weight, more preferably from 5 to 30 parts by weight of the emulsifier having an HLB of 6 to 10, based on 100 parts by weight of the metal salt, from the viewpoint of exhibiting the desired effects of the present invention.

In addition, the composition of the present invention may further contain as other components a hydrophilic surfactant component. In the case where such a component is contained, a highly favorable dispersibility is attained by the action of the hydrophilic surfactant component, thereby further improving the dispersibility of the composition of the present invention when the composition is added and mixed with foods or beverages, for example.

The surfactant component described above includes other surfactant components having an HLB exceeding 10, for example, metallic soaps such as sodium oleate; alkyl ether surfactants such as nonyl phenyl ether; polyoxyethylene adduct-type surfactants such as Tween; emulsifiers for food, such as sucrose fatty acid esters, glycerol fatty acid esters, phospholipids, enzymatically decomposed lecithins, propylene glycol fatty acid esters and sorbitol fatty acid esters; and saponin compounds derived from quillaia and yucca form; and the like. Among them, it is more preferable that a highly hydrophilic surfactant component, including polyglycerol fatty acid esters, polyoxyethylene adduct-type surfactants, sucrose fatty acid esters, enzymatically decomposed lecithins and the like, is used in combination with the emulsifier of the present invention.

The content of the other components in the composition of the present invention is not particularly limited, as long as the desired effects of the present invention are not inhibited. It is desired that the content is preferably 30 parts by weight or less, more preferably 10 parts by weight or less, based on 100 parts by weight of the emulsifier having an HLB of 6 to 10, from the viewpoint of allowing for the formation on the surface of the fine particles of the metal salt the above-mentioned adsorption layer of the emulsifier having an HLB of 6 to 10 which can sufficiently suppress secondary aggregation of the fine metal particles in the composition of the present invention.

In addition, as the other components, water may be contained as appropriate. Water is not particularly limited, and includes, for example, tap water, distilled water, ion-exchanged water and the like.

The composition of the present invention can be prepared as described below. For instance, the above-mentioned fine particles of the metal salt are dispersed in water and, if desired, the fine particles are ground by means described above to an average particle size within the above-mentioned desired range. To the resulting dispersion of the fine particles is added the above-mentioned emulsifier, and the mixture is heated to a temperature equal to or higher than the melting point of the emulsifier or to a temperature such that the emulsifier is dispersed. Next, the resulting mixture is homogenized, thereafter further heated if desired, and then kept for aging. On the other hand, the above emulsifier is added to water, heated to a temperature equal to or higher than the melting point of the emulsifier or to a temperature such that the emulsifier is dispersed and, if desired, homogenized, to prepare an emulsifier preparation. To this are added and mixed the above-mentioned fine particles of the metal salt, and the resulting mixture is homogenized thereafter further heated if desired, and then kept for aging, in the same manner as above. Incidentally, as the metal salt, fine particles of a metal salt obtained by the method for forming salt by neutralization may be used. The composition of the present invention can also be obtained by preparing the metal salt in water by the method for forming salt by neutralization in the simultaneous presence of the emulsifier in the dissolved state or the dispersed state. The other components mentioned above may appropriately be added and mixed at any timepoint in the step of preparing the composition of the present invention. The compositions of the present invention prepared according to these processes are generally obtained as a dispersion of fine metal particles, and a suitable solid content of the dispersion is about 1 to 20% by weight.

Incidentally, the process for preparing the composition of the present invention is not limited to those exemplified herein. The process for preparing the composition is not particularly limited, as long as the composition of the present invention, which can exhibit the desired effect, is obtained. The order of formulating the metal salt, the emulsifier and the like, and the method of mixing these components can be appropriately selected.

The composition of the present invention can be obtained as described above. Further, to the composition, a mucopolysaccharide having a polymer network structure, such as gum arabic, a soy polysaccharide, gelatin, pectin, sodium alginate, xanthan gum, carrageenan, dextrin, modified starch and modified cellulose may be added and mixed therewith. The amount of the mucopolysaccharide formulated is preferably 0.5 to 500 parts by weight, more preferably 1 to 100 parts by weight, even more preferably 5 to 30 parts by weight, based on 100 parts by weight of the fine metal particles. When the mucopolysaccharide is added, the fine particles are to be supported in the polymer network structure. As a result, the dispersion stability of the composition of the present invention can be further improved, which is preferable.

In addition, if desired, the compositions of the present invention obtained as a dispersion by the methods described above may be appropriately dried to be made into powder by the known methods. In that case, secondary aggregation of the fine metal particles may partially occur because of the water loss in the drying step. On the other hand, as described above, when the fine metal particles contained in the composition of the present invention are supported in the polymer network structure of a mucopolysaccharide, there are obtained not only the steric hindrance effect by the molecules of the emulsifier in the fine particles but also the steric hindrance effect by the above polysaccharide, thereby preventing the particles from being coarse mass, which is preferable.

Further, as one embodiment of the present invention, there is provided a food or beverage comprising the composition of the present invention. The food or beverage can be prepared, for instance, by adding the composition of the present invention to ready-made food or beverage, or adding in advance the composition of the present invention to the raw materials to be used or simultaneously formulating the composition of the present invention during the step of preparing the food or beverage. Also, the foods of the present invention can be prepared by adding the composition of the present invention together with the raw materials when cooking foods (or beverages in some cases). The timepoint when the composition of the present invention is added to foods or beverages, and method of mixing the composition of the present invention with foods or beverages are not particularly limited, as long as foods or beverages can be obtained which can exhibit the desired effects of the present invention.

The content of the composition of the present invention in the foods or beverages of the present invention is not particularly limited. The content may be an amount of the composition sufficient for supplement of deficient mineral, and may be appropriately determined according to the composition of the foods or beverages in which the composition of the present invention is to be incorporated, or the subject individual who takes the foods or beverages. Generally, the content of the composition of the present invention in the foods or beverages of the present invention is preferably 0.01 to 5% by weight, more preferably 0.02 to 3% by weight.

The foods or beverages in which the composition of the present invention can be incorporated are not particularly limited. The foods or beverages include, for example, foods such as wheat flour processed foods typically exemplified by cookies, bread, noodles, and the like; rice processed foods such as rice gruel and rice cooked with meat and vegetables; processed meet products and processed fish meet products; drinks such as soft drinks, milk-based beverages, soda pops and alcoholic beverages. These foods or beverages contain a water-insoluble metal salt such as calcium phosphate, magnesium phosphate and ferric pyrophosphate with excellent bioabsorbability. By taking these foods or beverages, nutrition enrichment of minerals such as calcium, magnesium and iron, which are tend to be deficient, can be easily effected. Conventionally, in liquid foods, mostly beverages, addition of water-insoluble metal salt has had a very restricted application due to precipitation of mineral component. However, according to the present invention, nutrition enrichment of minerals in a chemically stable form can be effected without impairing the external appearance or flavors of the foods. For instance, by preparing a composition of the present invention comprising calcium phosphate, magnesium phosphate, ferric pyrophosphate and the like each independently or in admixture of two or more kinds, and then adding the composition to a beverage such as milk, a lactic acid beverage, a soft drink or a soda pop, beverages and the like enriched in calcium, magnesium and/or iron with excellent stability can be prepared.

Incidentally, the composition of the present invention can also be added to feeds for livestocks, household pets and the like, and sufficiently contribute to nutrition enrichment of minerals for animals taking such feeds. The feeds include any known feeds such as feeds for livestocks. In particular, the composition can be preferably used for feeds for household pets. The content of the composition of the present invention in a feed is not particularly limited, and may be an amount of the composition sufficient for supplement of deficient mineral. The content may be appropriately determined according to the composition of a feed in which the composition of the present invention is to be incorporated and the subject animal which is feeded. Generally, the content of the composition of the present invention in the feed is preferably 0.01 to 5% by weight, more preferably 0.02 to 3% by weight.

Such feed can be appropriately prepared according to the above-mentioned method for preparing the foods or beverages of the present invention, or the known methods for preparing feeds.

In addition, the fine metal particles contained in the composition of the present invention are excellent in dispersion stability in a liquid component. Therefore, a water-insoluble metal salt call be maintained in an excellently dispersed state in a liquid component when the composition is used. Accordingly, there can be provided various household goods and industrial products which are highly excellent in terms of external appearance, availability and the like, by using the composition of the present invention.

The above-mentioned household goods include, for example, cosmetics containing the composition of the present invention. Specifically, the cosmetics include, for example, lotion; milky lotion; bathing agents; detergents such as cleansing agents; dentifrices, and the like. Particularly in bathing agents, a bathtub may be damaged in some cases due to precipitation of metal salts, such as calcium carbonate, which are used as a main ingredient, however, in the case of a bathing agent containing the composition of the present invention, a damage to a bathtub is suppressed because the fine metal particles contained in the composition of the present invention are excellent in dispersion stability in a liquid component so that the particles will not precipitate in the bathing agent.

Also, the industrial products include, for example, films for agricultural purposes, sheet materials for walls or floors, fire-proofing agents to be added to resins, and the like. For these products, the composition of the present invention containing a metal salt selected from, for example, calcium carbonate, barium sulfate, magnesium hydroxide and zinc hydroxide is preferably used. In such products, these minerals disperse stably in the resinous base materials, so that the functional properties such as physical strength after molding, smoothing of the surface and fire-proofing properties, can be improved.

These products can be appropriately manufactured according to the known manufacturing methods by adding and formulating to the raw materials and the like the composition of the present invention in an amount sufficient to exhibit the desired effects for individual products in accordance with the composition of the components of the subject to be applied. Generally, the content of the composition of the present invention in the product is preferably 0.01 to 5% by weight, more preferably 0.02 to 3% by weight.

Next, the present invention will be described in more detail by the Examples, without intending to limit the present invention thereto.

EXAMPLES

Example 1

A dispersion prepared by dispersing 4 kg of ferric pyrophosphate (manufactured by Tomita Yakuhin Kogyo K. K.) in 94.9 kg of deionized water was placed in a Dyno-Mill, and the particles of ferric pyrophosphate were physically ground, to prepare a slurry containing the ground particles having an average particle size of about 0.25 μm. To the slurry was added and dissolved therein 1.1 kg of diglycerol monolaurate (trade name: "SUNSOFT Q-12 D"; HLB=9; monoester content: 80% by weight; specific gravity: 0.9; manufactured by Taiyo Kagaku Co., Ltd.). The solution was heated until the temperature thereof was 45° C., and then subjected to a treatment in a homogenizer for 15 minutes. Thereafter, the temperature of the solution was further increased to 75° C., and then kept at 75° C. for 10 minutes. Following the above procedure, a ferric pyrophosphate dispersion composition having a solid content of 4% by weight (Inventive Product A) was obtained (average particle size of fine metal particles: about 0.25 μm). The dispersion was filled in a clear container, and stored at normal temperatures (25° C.).

Example 2

A dispersion prepared by dispersing 4 kg of ferric pyrophosphate (manufactured by Tomita Yakuhin Kogyo K. K.) in 93 kg of deionized water was placed in a Dyno-Mill, and the particles of ferric pyrophosphate were physically ground, to prepare a slurry containing the ground particles having an average particle size of about 0.25 μm. To the slurry was added and dissolved therein an emulsion agent preparation prepared by mixing and dissolving in 1.7 kg of deionized water previously heated to 65° C. 1.2 kg of diglycerol monomyristate (trade name: "SUNSOFT Q-14 D"; HLB=8.3, monoester content: 75% by weight; specific gravity: 0.9; manufactured by Taiyo Kagaku Co., Ltd.) and 0.1 kg of pentaglycerol monolaurate (A-121E; HLB=13; specific gravity: 0.9; manufactured by Taiyo Kagaku Co., Ltd.). The solution was heated until the temperature thereof was 45° C., and then subjected to a treatment in a homogenizer for 15 minutes. Thereafter, the temperature of the solution was further increased to 75° C., and then kept at 75° C. for 10 minutes. Following the above procedure, a ferric pyrophosphate dispersion composition having a solid content of 4% by weight (Inventive Product B) was obtained (average particle size of fine metal particles: about 0.25 µm). The dispersion was filled in a clear container, and stored at normal temperatures.

Example 3

In 60 kg of ion-exchanged water was dissolved 13 kg of ferric chloride hexahydrate to prepare an iron solution. To a solution prepared by dissolving 20 kg of tetrasodium pyrophosphate decahydrate in 500 kg of ion-exchanged water was gradually added the above iron solution with stirring. The pH of the resulting mixture was adjusted to 3 using a handy pH meter manufactured by HORIBA, Ltd. After forming of the salt of ferric pyrophosphate by neutralization reaction was terminated, the resulting reaction mixture was subjected to solid-liquid separation by centrifugation (3000×g, for 5 minutes), and ferric pyrophosphate of the solid phase portion was collected. The ferric pyrophosphate was resuspended in ion-exchanged water, to give a slurry containing particles (average particle size: about 0.21 µm) of ferric pyrophosphate with a solid content of 4% by weight. Fifty kilograms of the slurry was transferred to another stainless beaker, and 0.8 kg of diglycerol monopalmitate (HLB=7.3, monoester content: 80% by weight; specific gravity: 0.9; manufactured by Taiyo Kagaku Co., Ltd.) was added and dissolved therein. The solution was heated until the temperature thereof was 45° C., and then subjected to a treatment in a homogenizer for 15 minutes. Thereafter, the temperature of the solution was further increased to 75° C., and then kept at 75° C. for 10 minutes. Following the above procedure, a ferric pyrophosphate dispersion composition having a solid content of 4% by weight (Inventive Product C) was obtained (average particle size of fine metal particles: about 0.25 µm). The dispersion was filled in a clear container, and stored at normal temperatures.

Comparative Example 1

In 60 kg of ion-exchanged water were dissolved 13 kg of ferric chloride hexahydrate and 0.3 kg of an enzymatically decomposed lecithin (trade name: "SUNLECITHIN A"; HLB=15; specific gravity: 0.9; manufactured by Taiyo Kagaku Co., Ltd.) to prepare an iron solution. To a solution prepared by dissolving 20 kg of tetrasodium pyrophosphate decahydrate in 500 kg of ion-exchanged water was gradually added the above iron solution with stirring. The pH of the resulting mixture was adjusted to 3 using a handy pH meter manufactured by HORIBA, Ltd. After forming of the salt of ferric pyrophosphate by neutralization reaction was terminated, the resulting reaction mixture was subjected to solid-liquid separation by centrifugation (3000×g, for 5 minutes), and ferric pyrophosphate of the solid phase portion was collected. The ferric pyrophosphate was resuspended in ion-exchanged water, to give a slurry containing particles (average particle size: about 0.21 µm) of ferric pyrophosphate with a solid content of 4% by weight. Fifty kilograms of the slurry was transferred to another stainless beaker, and 0.4 kg of decaglycerol monomyristate (HLB=14; specific gravity: 0.9; manufactured by Taiyo Kagaku Co., Ltd.) was added and dissolved therein. The solution was heated until the temperature thereof was 45° C., and then subjected to a treatment in a homogenizer for 15 minutes. Thereafter, the temperature of the solution was further increased to 75° C., and then kept at 75° C. for 10 minutes. Following the above procedure, a ferric pyrophosphate dispersion composition having a solid content of 4% by weight (Comparative Product A) was obtained (average particle size of fine metal particles: about 0.28 µm). The dispersion was filled in a clear container, and stored at normal temperatures.

Comparative Example 2

A ferric pyrophosphate dispersion composition having a solid content of 4% by weight (Comparative Product B) was obtained (average particle size of fine metal particles: about 0.25 µm) in the same manner as in Example 2, except that an emulsion agent preparation obtained by dissolving in 1.2 kg of deionized water 1 kg of a sugar ester (trade name: "RYOTO SUGAR ESTER S-1670"; HLB=16; manufactured by Mitsubishi-Kagaku Foods Corporation) and 0.8 kg of polyoxyethylene (20) sorbitan monolaulate (trade name: "TL-10"; HLB=16.9; specific gravity: 0.9; manufactured by Hikari Chemicals) was used in place of 3 kg of the emulsion agent preparation of diglycerol monomyristate and pentaglycerol monolaurate in Example 2. The dispersion was filled in a clear container, and stored at normal temperatures. Incidentally, the (20) in the polyoxyethylene (20) sorbitan monolaulate indicates the number of moles of ethylene oxide added.

Comparative Example 3

A ferric pyrophosphate dispersion composition having a solid content of 4% by weight (Comparative Product C) was obtained (average particle size of fine metal particles: about 0.25 µm) in the same manner as in Example 3, except that 0.8 kg of a gum arabic (manufactured by Colloid Naturel Japan) was used in place of 0.8 kg of the diglycerol monopalmitate in Example 3. The dispersion was filled in a clear container, and stored at normal temperatures.

Test Example 1

For the Inventive Products A to C of Examples 1 to 3 and the Comparative Products A to C of Comparative Examples 1 to 3, a comparison was made of the bioabsorbability of the mineral component (iron) contained therein.
(Assaying of Serum Iron Concentration Following Administration of Test Sample)

As a test sample, the Inventive Products A to C and the Comparative Products A to C were individually used.

SD-male rats of 10 week old were divided in the groups administered with the respective Inventive Products A to C and Comparative Products A to C (ten rats per group). A group given water served as a control. The rats of individual groups were fasted for 18 hours. Thereafter, each of the Inventive Products A to C and Comparative Products A to C was dissolved in distilled water. The resulting solution made into concentrations of 2 mg iron/kg equivalency for one rat was forcibly orally administered to a rat with a probe. The water group was given water orally in the same manner as above.

Following administration, blood was drawn from jugular after the passage of time of 0.5, 1, 2, 4, or 8 hours, and sera were immediately separated from each of drawn blood samples. Thereafter, the iron in sera (serum iron) was measured according to a standard method of International Committee for Standardization in Hematology. Table 1 shows the results of measurement (average value for ten rats) and the area under a curve indicating the total amount of serum iron at 0.5 to 8 hours following administration of a test sample or water for the individual groups. Also are shown a maximum value of serum iron concentration and the timepoint at which the concentration reached a maximum in this study. Further, a graph showing changes in serum iron concentration over time in the individual groups, plotted based on the above results of measurement, is shown in FIG. 1.

TABLE 1

| Group | Maximum Serum Iron Concentration | Serum Iron Concentration at Each Time Following Administration | | | | | Area Under Curve of Serum Iron |
|---|---|---|---|---|---|---|---|
| | | 0.5 h | 1 h | 2 h | 4 h | 8 h | |
| Inventive Product | | | | | | | |
| A | 403 (2) | 256 | 398 | 403 | 292 | 136 | 2317 |
| B | 417 (2) | 241 | 387 | 417 | 281 | 198 | 2231 |
| C | 399 (2) | 239 | 379 | 399 | 276 | 165 | 2356 |
| Comparative Product | | | | | | | |
| A | 347 (2) | 275 | 335 | 347 | 233 | 134 | 1752 |
| B | 323 (0.5) | 323 | 298 | 261 | 192 | 121 | 1482 |
| C | 179 (1) | 154 | 179 | 135 | 127 | 116 | 1057 |
| Water | 112 | 126 | 114 | 108 | 113 | 109 | 879 |

Note:
The unit of the concentration and the area under a curve of serum iron is "µg/dL".
The values in parentheses indicate the time (hour) to reach a maximum serum iron concentration following administration.

From the results shown in Table 1 and FIG. 1, for the changes in serum iron concentration over time in the case where the Comparative Products were administered, the serum iron concentration reached a maximum at 0.5 to 1 hour or so following administration (except Comparative Product A), and then gradually declined. On the other hand, in the case of the Inventive Products, the serum iron concentration reached a maximum at about 2 hours following administration, and then gradually declined. In addition, based on the data in Table 1, a test of significance was conducted by using the values representing the total amounts of the iron taken into the body, which were calculated as the area under a curve, for the Inventive Products and the Comparative Products. As a result, in the case where the Inventive Products were administered, the values were significantly high at a risk rate of 5%, as compared to the case where the Comparative Products were administered.

It can be seen from these results that the absorbability of the iron contained in the Inventive Products A to C is evidently increased, as compared to that contained in the Comparative Products A to C. It can be also seen that the time to reach a maximum serum iron concentration following administration is longer and the serum iron concentration at this time is higher, and thus high serum iron concentrations are maintained for a longer period of time in the Inventive Products A to C than the Comparative Products A to C, so that the Inventive Products A to C exhibit excellent sustained-release property.

The Comparative Product A shows a sustained-release behavior similar to that of the Inventive Products, which is presumably due to the effect by the enzymatically decomposed lecithin. However, since the enzymatically decomposed lecithin is a hydrophilic emulsifier, its affinity to the cell membrane of the intestinal epithelial cells would be low. In the results for the Comparative Product A, the total amount of serum iron at 0.5 to 8 hours following administration is low, as compared with the Inventive Products. According to the results, it can be said that the absorbability of iron contained in the Inventive Products, that is, the bioavailability of the iron is high, as compared with the Comparative Product A.

Test Example 2

For the Inventive Products A to C of Examples 1 to 3 and the Comparative Products A to C of Comparative Examples 1 to 3, a comparison was made of the storage stability.
(Evaluation of Storage Stability)
The Inventive Products and Comparative Products were stored with leaving them at rest at normal temperatures. The extent of occurrence of separation and precipitation of the constituents in the dispersion was visually observed at regular intervals for 3 months from the time immediately after the preparation, and the extent of occurrence was recorded according to the following evaluation criteria. The results are shown in Table 2.
[Evaluation Criteria]
   o: No constituent separation, with no precipitation at the bottom of the container;
   Δ: Slight constituent separation is found, with a small quantity of precipitation found at the bottom of the container; and
   x: There is constituent separation occurred, with a large quantity of precipitation found at the bottom of the container.

TABLE 2

| | Storage Time | | | |
|---|---|---|---|---|
| | Immediately After Preparation | 1 Week Later | 1 Month Later | 3 Months Later |
| Inventive Product | | | | |
| A | o | o | o | o |
| B | o | o | o | Δ |
| C | o | o | o | o |
| Comparative Product | | | | |
| A | Δ | X | X | X |
| B | o | Δ | X | X |
| C | o | o | Δ | X |

It can be seen from the result in Table 2 that the dispersions of the Inventive Products A to C exhibit excellent storage stability, with substantially no occurrence of separation and precipitation of the constituents during the storage, while the dispersions of the Comparative Products A to C are poor in storage stability, as separation and precipitation of the constituents easily occurs and a large quantity of precipitation is found at the bottom of the container during the storage. It is presumed that the difference as described above is ascribed to the fact that the dispersibility and dispersion stability of the fine metal particles contained in the Inventive Products are higher than those in the Comparative Products.

Examples 4 to 6

The Inventive Products A to C of Examples 1 to 3 were individually added to 100 g of commercially available milk so that ferric pyrophosphate was contained in an amount of 12 mg. Next, the mixtures were homogenized at a pressure of 16.7 MPa using a high-pressure homogenizer, then subjected to a sterilization treatment at ultra high temperature in short time at 145° C. for 2 seconds (UHT processing), and cooled, to prepare an iron-enriched milk.

Test Example 3

For the Inventive Products A to C of Examples 1 to 3 and the Comparative Products A to C of Comparative Examples 1 to 3, a comparison was made of the dispersion stability in milk.
(Evaluation of Dispersion Stability in Milk)

The iron-enriched milks of Examples 4 to 6 prepared using the respective Inventive Products A to C of Examples 1 to 3, and the comparative milks A to C prepared as descried in Examples 4 to 6 using the respective Comparative Products A to C of Comparative Examples 1 to 3 were individually filled in a clear container, and stored with leaving them at rest at normal temperatures. The milks were visually observed for extent of occurrence of separation and precipitation of the constituents in the milk, at regular intervals, for 7 days from the time immediately after the preparation, and the extent of occurrence was recorded according to the following evaluation criteria. The results are shown in Table 3.
[Evaluation Criteria]
- o: No constituent separation, with no precipitation at the bottom of the container;
- Δ: Slight constituent separation is found, with a small quantity of precipitation found at the bottom of the container; and
- x: There is constituent separation occurred, with a large quantity of precipitation found at the bottom of the container.

TABLE 3

| | Storage Time | | |
|---|---|---|---|
| | Immediately After Preparation | 3 Days Later | 7 Days Later |
| Inventive Product | | | |
| A | o | o | o |
| B | o | o | o |
| C | o | o | o |
| Comparative Product | | | |
| A | Δ | X | X |
| B | o | Δ | X |
| C | o | o | Δ |

It can be seen from the result in Table 3 that the milks in which the Inventive Products A to C are added exhibit excellent storage stability, with substantially no occurrence of separation and precipitation of the constituents during the storage, while the milks in which the Comparative Products A to C are added are poor in storage stability, as separation and precipitation of the constituents easily occurs and a large quantity of precipitation is found at the bottom of the container during the storage. It is presumed that the difference as described above is ascribed to the fact that the dispersibility and dispersion stability of the fine metal particles contained in the Inventive Products are higher than those in the Comparative Products.

Example 7

A dispersion prepared by dispersing 4 kg of ferric pyrophosphate (manufactured by Tomita Yakuhin Kogyo K. K.) in 93.5 kg of deionized water was placed in a Dyno-Mill, and the particles of ferric pyrophosphate were physically ground, to prepare a slurry containing the ground particles having an average particle size of about 0.25 μm. To the slurry was added and dissolved therein 1.5 kg of diglycerol monolaurate (trade name: "SUNSOFT Q-12 D"; HLB=9; manufactured by Taiyo Kagaku Co., Ltd.). The solution was heated until the temperature thereof was 45° C., and then subjected to a treatment in a homogenizer for 15 minutes. Thereafter, the temperature of the solution was further increased to 75° C., and then kept at 75° C. for 10 minutes. Further, in the resulting mixture (3 kg of fine metal particles) were dissolved 8 kg of dextrin and 2 kg of water-soluble soy polysaccharide, and the resulting mixture was pulverized by spray drying, to give a powder composition containing 25% by weight of ferric pyrophosphate (average particle size of fine metal particles: about 0.25 m). The composition was excellent in dispersibility in deionized water, and the storage stability of the resulting dispersion was excellent.

Example 8

Three kilograms of calcium hydroxide was dispersed in 300 kg of ion-exchanged water. To the resulting dispersion was gradually added with stirring a solution obtained by diluting 3.3 kg of a 85% by weight solution of phosphoric acid with ion-exchanged water to a total quantity of 100 kg. The pH of the resulting mixture was adjusted to 5 using a handy pH meter manufactured by HORIBA, Ltd. After forming of the salt of calcium phosphate by neutralization reaction was terminated, the resulting reaction mixture was subjected to solid-liquid separation by centrifugation (3000×g, for 5 minutes), and 4.1 kg (dry weight basis) of calcium phosphate of the solid phase portion was collected. The calcium phosphate was resuspended in ion-exchanged water, to give a slurry containing particles (average particle size: about 0.30 μm) of calcium phosphate with a solid content of 10% by weight. To 10 kg of the slurry was added and dissolved therein 0.1 kg of diglycerol monolaurate (trade name: "SUNSOFT Q-12 D"; HLB=9; manufactured by Taiyo Kagaku Co., Ltd.). The solution was heated until the temperature thereof was 45° C., and then subjected to a treatment in a homogenizer for 15 minutes. Thereafter, the temperature of the solution was further increased to 75° C., and then kept at 75° C. for 20 minutes. The resulting calcium phosphate dispersion composition (average particle size of fine metal particles: about 0.30 μm) was filled in a clear container, and stored with leaving it at rest for 1 month at normal temperatures. As a result, the composition was excellent in dispersion stability, with no occurrence of separation and precipitation of the constituents.

Comparative Example 4

A calcium phosphate dispersion composition was obtained (average particle size of fine metal particles: about 0.25 μm) in the same manner as in Example 8, except that decaglycerol monostearate (trade name: "SUNSOFT Q-18 S"; HLB=12; specific gravity: 0.9; manufactured by Taiyo Kagaku Co., Ltd.) in place of the diglycerol monolaurate. The resulting composition was filled in a clear container, and stored with leaving it at rest for 1 week at normal temperatures. As a result, a large quantity of precipitation was found at the bottom of the container.

Example 9

A solution obtained by diluting 2.7 kg of a 85% by weight solution of phosphoric acid with ion-exchanged water to a total quantity of 100 kg was gradually added with stirring to a solution obtained by adding 2 kg of magnesium hydroxide to 300 kg of ion-exchanged water, and then further adding and dissolving therein 2 kg of diglycerol monocaprate (trade name: "SUNSOFT Q-10 D"; HLB=9.5; monoester content: 85% by weight; specific gravity: 0.9; manufactured by Taiyo Kagaku Co., Ltd.). The pH of the resulting mixture was adjusted to 8 using a handy pH meter manufactured by HORIBA, Ltd. After forming of the salt of magnesium phosphate by neutralization reaction was terminated, the resulting reaction mixture was subjected to solid-liquid separation by centrifugation (3000×g, for 10 minutes), and 4 kg (dry weight basis) of magnesium phosphate of the solid phase portion was collected (average particle size of fine metal particles: about 0.31 μm). The magnesium phosphate was resuspended in ion-exchanged water, to give a magnesium phosphate dispersion composition having a solid content of 10% by weight (20 parts by weight of an emulsifier were contained based on 100 parts by weight of the metal salt). The resulting composition was filled in a clear container, and stored with leaving it at rest for 1 month at normal temperatures. As a result, the composition was excellent in dispersion stability, with no occurrence of separation and precipitation of the constituents.

Comparative Example 5

A magnesium phosphate dispersion composition (20 parts by weight of an emulsifier were contained based on 100 parts by weight of the metal salt) was obtained (average particle size of fine metal particles: about 0.31 μm) in the same manner as in Example 9, except that a sucrose ester of a fatty acid (trade name: "RYOTO SUGAR ESTER S-1670," manufactured by Mitsubishi Chemical Corporation) was used in place of the diglycerol monocaprate. The resulting composition was filled in a clear container, and stored with leaving it at rest for 1 week at normal temperatures. As a result, a large quantity of precipitation was found at the bottom of the container.

INDUSTRIAL APPLICABILITY

According to the present invention, there is provided a mineral composition usable as a mineral supplement, which is excellent in bioabsorbability, or bioavailability, without producing coarse mass of mineral particles due to secondary aggregation, which is also excellent in handling during manufacturing as well as dispersibility and dispersion stability in aqueous phase, and which has substantially no influence on the taste, color, physical properties and the like of the foods and the like when added thereto.

The invention claimed is:

1. An aqueous composition, comprising:
   (1) a metal salt having a solubility product in water at 25° C. of $1.0 \times 10^{-7}$ or less,
   (2) an emulsifier having an HLB of 6 to 10, and
   (3) water,
   wherein the metal salt is dispersed in water;
   wherein the metal salt comprises fine particles having an average particle size of 0.05 to 1 μm;
   wherein the emulsifier comprises a diglycerol fatty acid ester and an amount of the emulsifier is 0.5 to 50 parts by weight, based on 100 parts by weight of the metal salt;
   wherein the emulsifier does not include enzymatically decomposed lecithins; and
   wherein a monoester content of the diglycerol fatty acid ester is 50% by weight or more.

2. A powder composition which is obtained by a process comprising drying the aqueous composition of claim 1.

3. The aqueous composition according to claim 1, wherein the metal salt is a salt of at least one member selected from the group consisting of calcium, magnesium, iron and zinc.

4. The aqueous composition according to claim 1, wherein the metal salt is selected from the group consisting of calcium carbonate, calcium phosphate, magnesium phosphate, magnesium oxide, ferric pyrophosphate, zinc hydroxide, zinc pyrophosphate, zinc oxide and dolomite having a $MgCO_3 \cdot CaCO_3$ composition.

5. The aqueous composition according to claim 1, wherein the HLB of the emulsifier is from 6 to 9.

6. The aqueous composition according to claim 1, wherein the HLB of the emulsifier is from 7 to 9.

7. The aqueous composition according to claim 1, wherein the amount of the emulsifier is from 1 to 40 parts by weight, based on 100 parts by weight of the metal salt.

8. The aqueous composition according to claim 1, wherein the amount of the emulsifier is from 5 to 30 parts by weight, based on 100 parts by weight of the metal salt.

9. The aqueous composition according to claim 1, wherein the monoester content of the diglycerol fatty acid ester is 70% by weight or more.

10. A food or beverage, comprising the aqueous composition of claim 1.

11. A food or beverage, comprising the powder composition of claim 2.

12. A food or beverage, comprising the aqueous composition of claim 3.

13. A food or beverage, comprising the aqueous composition of claim 4.

14. A food or beverage, comprising the aqueous composition of claim 5.

15. A food or beverage, comprising the aqueous composition of claim 6.

16. A food or beverage, comprising the aqueous composition of claim 7.

17. A food or beverage, comprising the aqueous composition of claim 8.

18. A food or beverage, comprising the aqueous composition of claim 9.

* * * * *